(12) United States Patent
Wistrand et al.

(10) Patent No.: US 8,815,210 B2
(45) Date of Patent: Aug. 26, 2014

(54) DIAGNOSTIC COMPOSITION COMPRISING PLASMA CATIONS HAVING SUPERIOR SAFETY PROFILE

(75) Inventors: Lars-Göran Wistrand, Oslo (NO); Mikkel Thaning, Oslo (NO); Ben Newton, Oslo (NO)

(73) Assignee: GE Healthcare AS, Oslo (NO)

( * ) Notice: Subject to any disclaimer, the term of this patent is extended or adjusted under 35 U.S.C. 154(b) by 102 days.

(21) Appl. No.: 13/497,641

(22) PCT Filed: Oct. 28, 2010

(86) PCT No.: PCT/EP2010/066351
§ 371 (c)(1),
(2), (4) Date: Mar. 22, 2012

(87) PCT Pub. No.: WO2011/051387
PCT Pub. Date: May 5, 2011

(65) Prior Publication Data
US 2012/0328522 A1     Dec. 27, 2012

(30) Foreign Application Priority Data
Oct. 29, 2009  (EP) .................... 09174413

(51) Int. Cl.
*A61K 49/00* (2006.01)
*A61K 49/04* (2006.01)
(52) U.S. Cl.
CPC ......... *A61K 49/0452* (2013.01); *A61K 49/0438* (2013.01)
USPC ............................................ 424/9.1; 424/9.4
(58) Field of Classification Search
USPC ........................................................ 424/9.1
See application file for complete search history.

(56) References Cited

U.S. PATENT DOCUMENTS 5,349,085 A * 9/1994 Hansen et al. ................. 564/153
5,993,780 A * 11/1999 Almen et al. ............... 424/9.452
8,066,970 B2 * 11/2011 Wynn et al. .................. 424/1.11

FOREIGN PATENT DOCUMENTS

| EP | 0390242 | 10/1990 |
| WO | 91/13636 | 9/1991 |
| WO | 2009/008734 | 1/2009 |

OTHER PUBLICATIONS

PCT/3P2010/06351 ISRWO Dated Feb. 16, 2011.

* cited by examiner

*Primary Examiner* — Michael G Hartley
*Assistant Examiner* — Melissa Perreira
(74) *Attorney, Agent, or Firm* — Yonggang Ji

(57) ABSTRACT

The present invention relates to a new diagnostic X-ray composition which exhibits a superior cardiac safety profile. The composition comprises a non-ionic iodinated dimer in a pharmaceutically acceptable carrier. More particularly, the invention provides a diagnostic composition comprising a Compound I, a pharmaceutically acceptable carrier, and dissolved therein a sodium compound and a calcium compound providing a sodium ion concentration of 40-50 mM and a calcium ion concentration of 0.1-0.7 mM. The invention also relates to methods of imaging using such diagnostic compositions.

15 Claims, 5 Drawing Sheets

Compound I

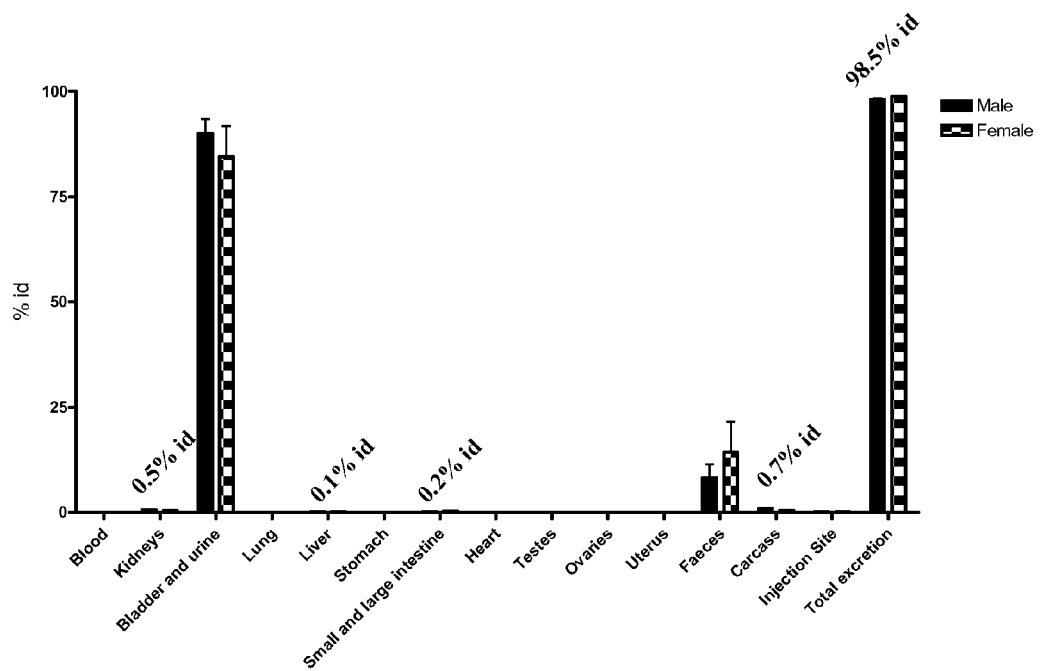
Figure 1. Comparison of the distribution of radioactivity in male and female Wistar rats at 48 hours post-administration of [$^{123}$I] labeled Compound I. Total excretion = sum of radioactivity in the bladder and urine plus faeces.

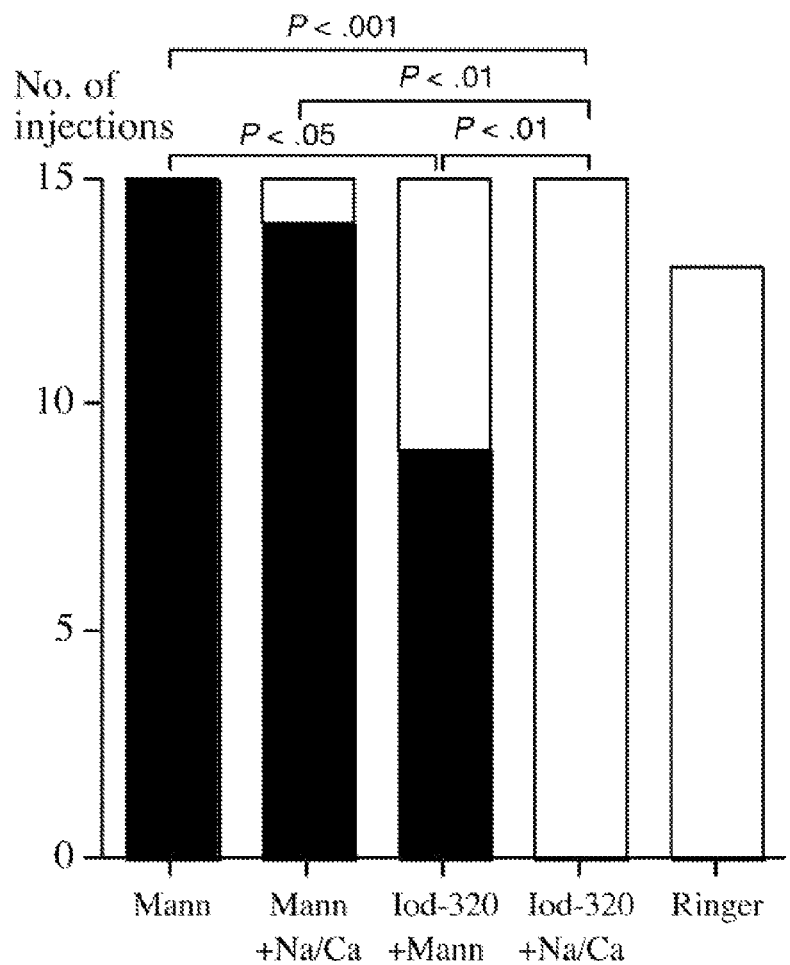

Figure 2. Frequency of ventricular fibrillation caused by injection of Mannitol (Mann; 275 mM), Mannitol + added sodium and calcium (Mann+Na/Ca; 240 mM mannitol, 19 mM NaCl and 0.3 mM $CaCl_2$), Iodixanol + Mannitol (Iod-320 + Mann; 320 mgI/ml Iodixanol and 50 mM Mannitol), VisipaqueTM (Iod-320; 320 mgI/ml Iodixanol, 19 mM NaCl and 0.3 mM $CaCl_2$) and Ringer solution (Ringer, Ringer acetate, KabiVitrum AB, Sweden). Black filling denotes VF, white filling denotes no VF. Data is taken from Chai et al.

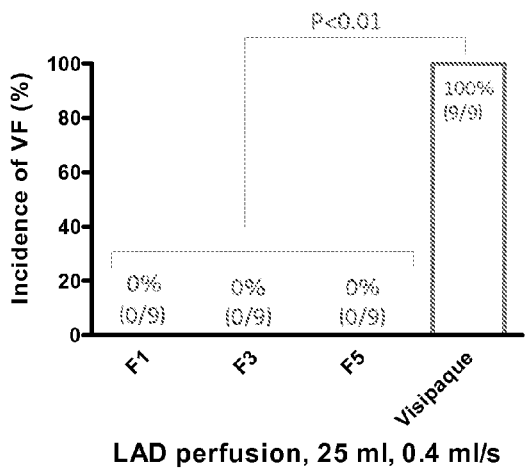
Figure 3. Frequency of ventricular fibrillation caused by injection of:
Compound I, 0.1 mM $CaCl_2$ (F1, 320 mgI/ml Compound I, 45 mM NaCl and 0.1 mM $CaCl_2$);
Compound I, 0.3 mM $CaCl_2$ (F3, 320 mgI/ml Compound I, 45 mM NaCl and 0.3 mM $CaCl_2$);
Compound I, 0.7 mM $CaCl_2$ (F5, 320 mgIml Compound I, 45 mM NaCl and 0.7 mM $CaCl_2$),
Visipaque
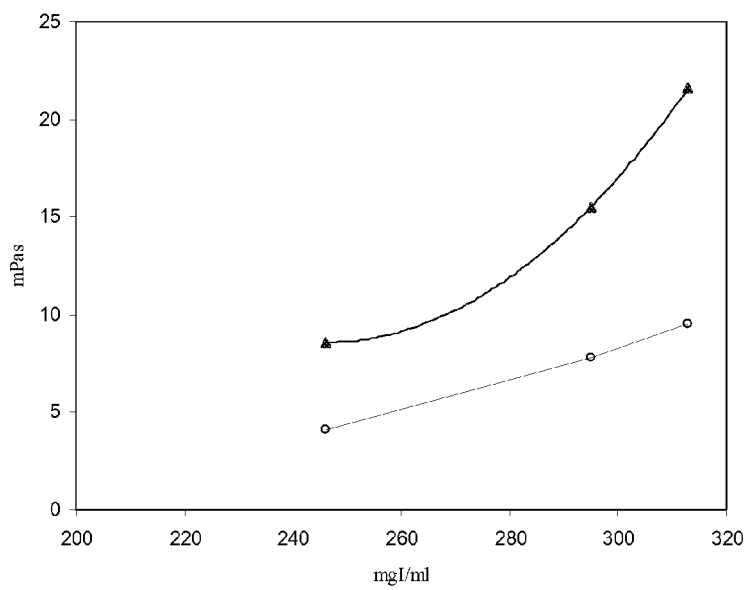
Figure 4. The viscosity of Compound I at 20°C (▲) and 37 °C (○) vs concentration.

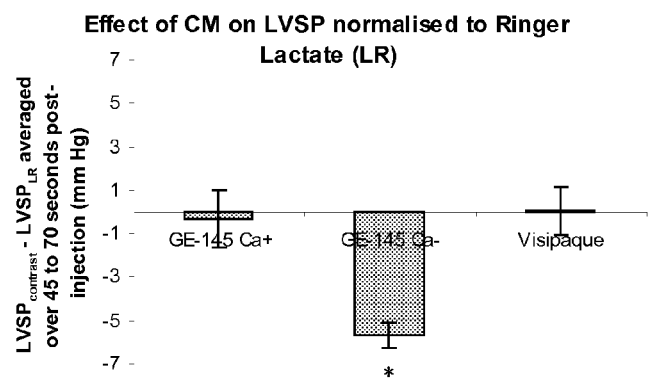

Figure 5. Effect of Compound I (with and without added Ca) and Visipaque on LVSP 45 to 70 seconds from the start of injection to the LAD of normal pigs normalised to Ringer Lacate (LR) injection. Injection volume was 25ml (0.4 ml/sec). "GE-145 Ca+" is a composition of Compound I containing 45 mM Na, 0.5 mM Ca, and "GE-145 Ca-" is a composition of Compound I containing 45 mM Na, and no added Ca.. Mean ± SEM. *= $p<0.05$ significant difference to GE-145 Ca+ using two-tailed Dunnett's test.

a)
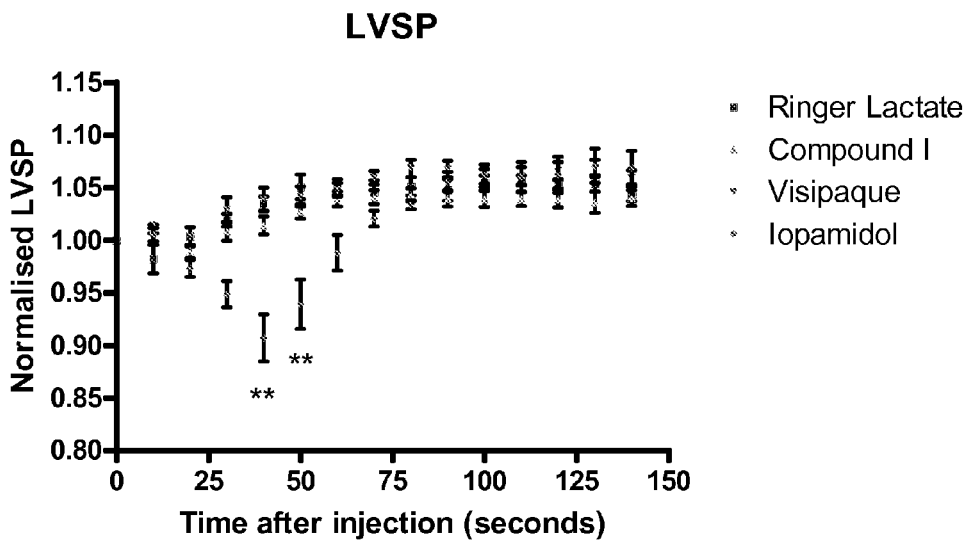
b)
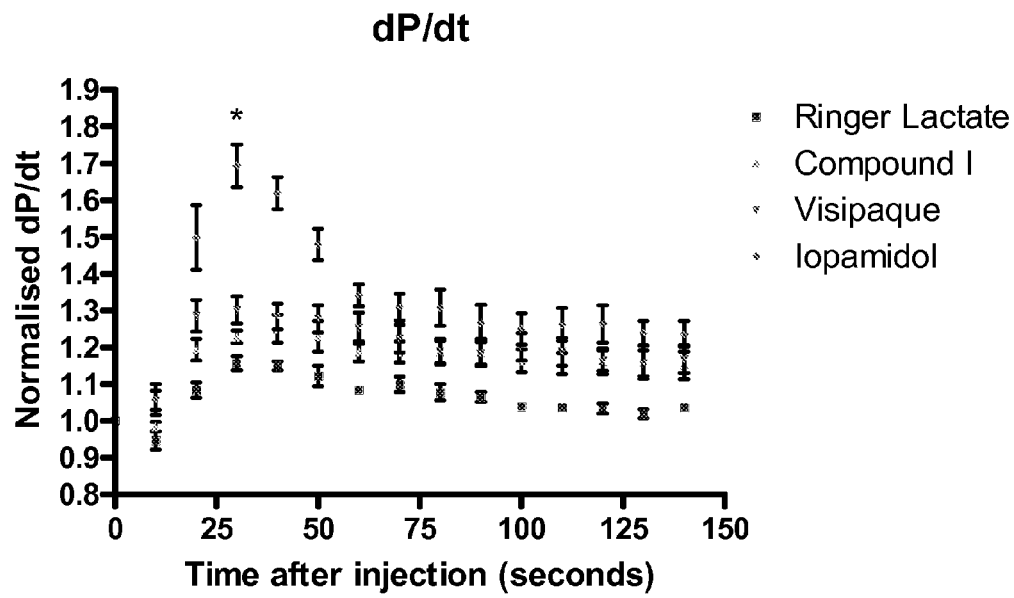
Figure 6. Effect on cardiovascular parameters following injection of 40 ml (5ml/sec) of Ringer Lactate, Compound I, Visipaque or Iopamidol to the LAD of normal pigs. a) Change in LVSP normalised to baseline. b) Change in dP/dt normalised to baseline. Mean ± SD. *=significant difference to Ringer Lactate, * $p<0.05$, **$p<0.01$ using 2-way ANOVA with Bonferroni post-test.

DIAGNOSTIC COMPOSITION COMPRISING PLASMA CATIONS HAVING SUPERIOR SAFETY PROFILE

This application is a filing under 35 U.S.C. 371 of international application number PCT/EP2010/066351, filed Oct. 28, 2010, which claims priority to European application number 09174413.6 filed Oct. 29, 2009, the entire disclosure of each of which is hereby incorporated by reference.

The present invention relates to a new diagnostic X-ray composition which exhibits a superior cardiac safety profile. The composition comprises a non-ionic iodinated dimer in a pharmaceutically acceptable carrier. The invention also relates to methods of imaging using such diagnostic composition.

All diagnostic imaging is based on the achievement of different signal levels from different structures within the body. Thus in X-ray imaging for example, for a given body structure to be visible in the image, the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedures, i.e. increased contrast can lead to increased spatial resolution. The diagnostic quality of images is strongly dependent on the inherent noise level in the imaging procedure, and the ratio of the contrast level to the noise level can thus be seen to represent an effective diagnostic quality factor for diagnostic images. Achieving improvement in such a diagnostic quality factor has long been and still remains an important goal.

In techniques such as X-ray, one approach for improving the diagnostic quality factor has been to introduce contrast enhancing materials formulated as contrast media into the body region being imaged. Thus for X-ray, early examples of contrast agents were insoluble inorganic barium salts which enhanced X-ray attenuation in the body zones into which they distributed. For the last 50 years the field of X-ray contrast agents has been dominated by soluble iodine containing compounds. Commercial available contrast media (CM) containing iodinated contrast agents are usually classified as ionic monomers such as diatrizoate (marketed e.g. under the trade mark Gastrografen™), ionic dimers such as ioxaglate (marketed e.g. under the trade mark Hexabrix™), nonionic monomers such as iohexol (marketed e.g. under the trade mark Omnipaque™), iopamidol (marketed e.g. under the trade mark Isovue™), iomeprol (marketed e.g. under the trade mark Iomeron™) and the non-ionic dimer iodixanol (marketed under the trade mark Visipaque™). The clinical safety of iodinated X-ray contrast media has continuously been improved over the recent decades through development of new agents; from ionic monomers (Isopaque™) to non-ionic monomers (e.g. Omnipaque™) and non-ionic dimers (e.g. Visipaque™). However, even the highly refined X-ray contrast media currently on the market exhibit a low degree of undesirable clinical side effects, such as Contrast Induced Nephropathy (CIN), adverse cardiac events, and delayed adverse reactions (DARs). Consequently, there is a clinical need for a new and safer X-ray contrast medium, especially with regards to diagnostic investigations involving patients where there is a high risk of these side effects.

The utility of the contrast media is governed largely by its toxicity, by its diagnostic efficacy, by adverse effects it may have on the subject to which the contrast medium is administered, and by the ease of production, storage and administration. The toxicity and adverse biological effects of a contrast medium are contributed to by the components of the formulation medium, i.e. of the diagnostic composition, e.g. the solvent or carrier as well as the contrast agent itself and its components such as ions for the ionic contrast agents and also by its metabolites.

The number of coronary arteriography procedures continues to increase consistent with the expanding capabilities of coronary interventions, including percutaneous transluminal coronary angioplasty, implantation of stents, and intracoronary administration of therapeutics. Over 70 million procedures, a majority of them cardiac related, are performed worldwide annually. Severe side effects caused by iodinated radiographic contrast media are rare, but can occur in high risk patients and during percutaneous coronary intervention.

In coronary arteriography the blood in the coronary arteries should ideally be completely replaced by a bolus of iodinated radiographic contrast media to maximize the attenuation of radiographs and thereby optimize diagnostic imaging. When contrast media replaces blood, the contrast media molecules cause chemotoxic and osmotic effects in the coronary vessels and also alterations in electrolyte concentrations, viscosity, and oxygen tension. These alterations may influence contractile force and cardiac rhythm and cause ventricular fibrillation (VF). Selective injection of contrast media into the coronary arteries induces regional electrophysiologic and hemodynamic effects. Serious ventricular arrhythmias, as well as cardiodepression, are known complications of coronary arteriography that may be related to the contrast media. WO91/13636 and WO90/11094, both of Nycomed AS (now GE Healthcare AS), are directed to X-ray contrast media and to their formulations including different salts. There are also numerous studies on the advantages of formulations of X-ray contrast agents with the inclusion of salts, mainly NaCl, in the literature. Studies have been performed on isolated hearts from rats (Jynge et al., Investigative Radiology 1993, 28, 20-25) and rabbits (Bååth et al, Investigative Radiology 1993, 28, 223-227), in dogs (Pedersen et al., Acad. Radiol. 1994, 1, 136-144) and in pigs. Of particular relevance is the study by Chai et al. (Acad. Radiol. 2004, 11, 583-593) where it is shown that a formulation of iodixanol containing 19 mM NaCl and 0.3 mM $CaCl_2$ exhibits a lower frequency of ventricular fibrillation than iodixanol alone.

Jacobsen et al., Investigative Radiology 1993; 28, 917-924 show that rapidly repeated injections of contrast media in dogs result in additive effects on inotropy and monophasic action potential whereas Ringer's solution had no effect. This was investigated to understand how angiography in clinical practice, where repeated injections are not uncommon to fill the whole coronary tree, can induce changes in cardiac parameters and lead to complications.

The current marketed formulation of iodixanol, 320 mgI/ml contains 19 mM sodium ions and 0.3 mM calcium ions (Visipaque™). This formulation has experimentally been shown to exhibit a superior cardiac safety profile as compared to iodixanol without added salts, mainly through in vivo studies in a cardiac pig model, but also through studies on isolated animal hearts. In similar studies it has been shown that iohexol also shows an increased cardiac tolerability when formulated with added salts, mainly NaCl.

WO 2009/008734 of GE Healthcare AS discloses a new class of compounds and their use as X-ray contrast agents. The compounds are dimers containing two linked iodinated phenyl groups. The bridge linking the two iodinated phenyl groups is a straight $C_3$ to $C_8$ alkylene chain optionally substituted by one to six —OH or $OCH_3$ groups. A range of compounds are covered by the general formula (I) of the application and many specific compounds are suggested.

Compound I, which is one specific dimeric X-ray contrast agent, falling within the formula I of WO2009/008734, has been found by the applicant to have favourable properties:

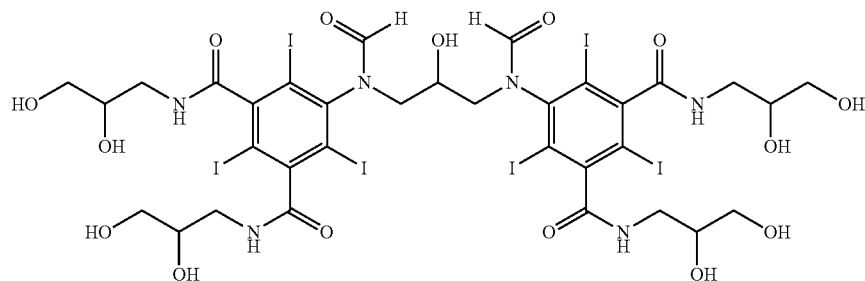 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound I: 5-[formyl-[3-[formyl-[3,5-bis(2,3-dihydroxypropylcarbamoyl)-2,4,6-triiodophenyl]amino]-2-hydroxypropyl]amino]-N,N'-bis(2,3-dihydroxypropyl)-2,4,6-triiodobenzene-1,3-dicarboxamide The applicant has now surprisingly identified a new diagnostic X-ray composition which exhibits a superior cardiac safety profile as compared to Visipaque™, as shown in similar in vivo studies as indicated above.

Thus, in a first aspect the invention provides a diagnostic composition comprising a compound I Partition Coefficient:
The hydrophilicity of Compound I, as determined through the partition between octanol and water, showed that Compound I is very hydrophilic with a logP of −4.28.

Viscosity:
The viscosity of compound I was determined at 20° C. and 37° C. at three different concentrations. The results are shown in FIG. 4. The viscosity at 320 mgI/ml and 20° C. is around 24 mPas.

Osmolality:
The osmolality of Compound I was determined at four different concentrations, 204, 254, 310 and 324 mgI/ml. The osmolality of Compound I at 320 mgI/ml is 136 mOsm/kg.

A new diagnostic X-ray composition which exhibits a superior cardiac safety profile as compared to Visipaque™, has been identified. In addition to the safety of the compound itself, i.e. the compound providing the contrast, the additional components of the diagnostic composition are crucial.

The study by Chai et al. shows that a formulation of iodixanol containing 19 mM NaCl and 0.3 mM $CaCl_2$ exhibits a lower frequency of ventricular fibrillation (VF) than iodixanol alone. This study was carried out in pigs where the medium was injected directly into the left coronary artery Compound I

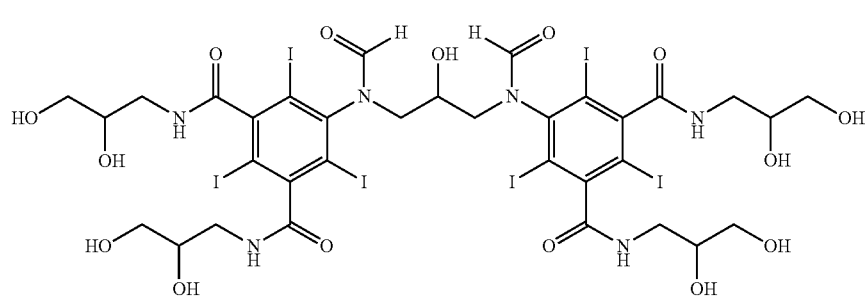

a pharmaceutically acceptable carrier;
and dissolved therein a sodium compound and a calcium compound providing a sodium ion concentration of 40-50 mM and a calcium ion concentration of 0.1-0.7 mM.

The physiochemical properties of Compound I are found below. Further information about the methods used, in addition to biodistribution and acute toxicity information, is provided in Example 1.

Protein Binding:
The binding of Compound I to human serum albumin (HSA) was determined using an equilibrium dialysis method. The binding of Compound I to human serum albumin was determined to be very low, 3.1±1.3%, confirming the negligible interaction of the substance with endogenous proteins.

(LCA) which had been previously occluded. No occurrence of ventricular fibrillation was observed on injection of Visipaque™. As part of the safety testing of Compound I, and identification of a formulation for this, formulations of Compound I were tested and compared with Visipaque™. Since in the previously published study (above) intracoronary injection of 20 ml iodixanol was carried out over a 40-s injection time and no instances of VF occurred, the injection volume was increased to 25 ml over a period of 62.5 s to increase the instances of VF for comparison purposes. In addition, the test and reference solutions were selectively injected into the left anterior descending coronary artery (LAD) in order to further increase the sensitivity of the model. At this high volume, even Visipaque exhibited a significant frequency of ventricular fibrillation, 100%. (FIG. 3). The experiments are outlined in Example 2.

To our surprise, the new X-ray contrast agent Compound I, when formulated in a diagnostic composition with as much as 40-50 mM NaCl and 0.1-0.7 mM CaCl$_2$, showed no occurrences of ventricular fibrillation (See FIG. 3 and Table 3 for details).

When comparing the results from the two different studies, an increase in the frequency of ventricular fibrillation from 0% to 100% was observed with Visipaque. However, even at the high dose, the dimeric X-ray contrast agent Compound I exhibited no ventricular fibrillation. The major difference is that Compound I was formulated with 45 mM NaCl in this study, which is significantly higher than that of Visipaque (19 mM). Although no significant effect was seen in ventricular fibrillation (VF) with calcium ion concentration between 0.1 and 0.7 mM, there was a significant reduction in systolic arterial pressure (SAP) and left ventricular systolic pressure (LVP) when less calcium was present (Table 2). These data indicate that the major factor influencing the frequency of ventricular fibrillation is the concentration of sodium chloride, while calcium has a significant effect on systolic arterial pressure and left ventricular systolic pressure (LVSP). Indeed, a study in normal pigs showed that whilst LAD injection of a composition of compound I containing 45 mM NaCl with no added CaCl$_2$ resulted in a reduction in LVSP 45 to 70 seconds after injection (mean of −5.7 mm Hg normalised to Ringer Lactate), injection of a composition of compound I containing 45 mM NaCl and 0.5 mM CaCl$_2$ maintained LVSP Lactate and Visipaque in this respect (a modest increase of up to 30%). It is considered that the presence and ratio of the electrolytes Sodium (Na) and Calcium (Ca) in the formulations of Compound I and Visipaque studied, which are closer to the Na/Ca balanced composition of Ringer Lactate and the interstitial fluid, contributed to a superior maintenance of cardiac function compared with that following Iopamidol injection, which contains no added electrolytes. The amounts and ratios of the electrolytes are provided in table 5 of Example 2b.

In a further embodiment of the invention the composition of the invention comprises a sodium compound providing a sodium ion concentration of 42-47 mM, and even more preferably a sodium ion concentration of 44-46 mM, and most preferably a sodium ion concentration of 45 mM.

In yet another embodiment of the invention the composition of the invention comprises a calcium compound providing calcium ion concentration of 0.3-0.6 mM, and even more preferably a calcium concentration of 0.4-0.5 mM and most preferably a calcium ion concentration of 0.5 mM.

In this aspect, the ratio between sodium ion concentration and calcium ion concentration should be between 57 and 500, such as between 63 and 117, more preferably between 70 and 156, more preferably between 85 and 115 and most preferably between 88 and 95.

In a second aspect, the invention provides a diagnostic composition comprising a compound I

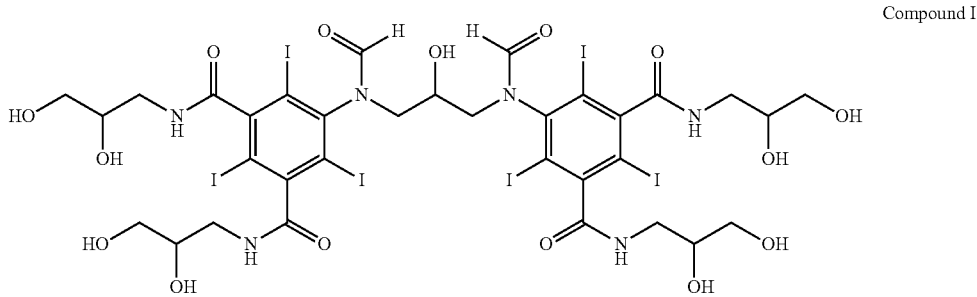 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound I in a manner similar to Visipaque (−0.3 and +0.1 mm Hg normalised to Ringer Lactate respectively) (Example 2b). In addition, injection of Iopamidol at the same rate and volume induced VF on every occasion (total of 9 injections in 3 pigs) between approximately 27 to 50 seconds after the start of injection (this limited any analysis of the LVSP response). These results further indicate that the presence of 0.5 mM CaCl$_2$ in the composition of Compound I is beneficial and limits any negative effects on LVSP in a manner similar to Visipaque. Furthermore, the added electrolytes present in the diagnostic composition of Compound I and Visipaque may lower the propensity to induce VF compared with Iopamidol which has no added electrolytes. The amounts and ratios of the electrolytes studied are provided in table 4 of Example 2b.

In a study of more rapid injections (40 ml, at 5 ml/sec) left ventricular systolic pressure was maintained and similar to that observed following Ringer Lactate and Visipaque administration when Compound I in a composition with 45 mM NaCl and 0.5 mM CaCl$_2$ was injected selectively to the LAD of normal pigs. In contrast Iopamidol injection, which contains no added electrolytes, induced a significant reduction in LVSP (Example 2c).

Furthermore, Iopamidol induced a substantial increase in dP/dt (69%) whereas Compound I was similar to Ringer a pharmaceutically acceptable carrier; and dissolved therein a sodium compound and a calcium compound wherein the ratio between sodium ion concentration and calcium ion concentration is between 40 and 45, and is preferably 43. This is to mirror the electrolyte concentrations of a Ringer lactate composition.

The sodium compound and the calcium compound of the composition may be provided in the form of salts, i.e. the compounds include physiologically tolerable counter ions, e.g. selected from the group of chloride, sulphate, phosphate and hydrogen carbonate. Preferably, the sodium compound is sodium chloride and the calcium compound is calcium chloride.

The pharmaceutically acceptable carrier is an aqueous solution, preferably pure water.

Sodium is essential for myocardial depolarization, which depends on an inward Na$^+$ current. We believe that adding 40-50 mM sodium ions, and preferably 45 mM NaCl, to Compound I brings it closer to the normal Na$^+$ interstitial concentration than iodixanol+19 mM Na$^+$/L. Thereby, Compound I might be more physiologic and better able to maintain the action potential of fast sodium channels, thus counteracting the "slow response" action potential caused by too little or no sodium.

Previous investigations have shown that adding small amounts of sodium (10-30 mmol/L) to nonionic contrast media may decrease the risk of ventricular fibrillation (VF) from these contrast media. However studies also show that the addition of more sodium to contrast media can also increase the negative inotropy, as indicted by reduced systolic arterial pressure/left ventricular systolic pressure (SAP/LVP). To maintain normal extracellular and intracellular sodium-calcium (Na—Ca) relationships, the addition of calcium to non-ionic contrast media reduces the negative inotropic effects. The key question though is how much calcium should be added to prevent the increase of the negative inotropy. The addition of 19 mM NaCl and 0.3 mM $CaCl_2$ to iodixanol 320 mg I/mL in the Visipaque formulation was considered optimal in order to minimize the physiological disturbances such as VF and increased negative inotropy during coronary angiography.

In our studies, the benefit of $CaCl_2$ to Compound I containing 45 mM NaCl was confirmed (Table 3). A formulation (F1) with 0.1 mM $CaCl_2$ induced significantly lower SAP and LVP than the formulation with 0.3 mM $CaCl_2$ (F3) or 0.7 mM $CaCl_2$ (F5) respectively. The formulation of Compound I with 0.3 mM $CaCl_2$ caused lower SAP than the formulation with 0.7 mM $CaCl_2$. It follows that adding calcium ions to the contrast media may counteract the negative inotropy caused by adding sodium.

However, there is a critical balance between sodium and calcium ions. Adding proper concentrations of sodium and calcium to nonionic contrast media decreases the risk of VF and reduces adverse effects on contractile force. Adding too much sodium decreases myocardial contractile force. This latter effect is counteracted by addition of Ca-ions. The formulation of Compound I, containing 45 mM NaCl and 0.7 mM $CaCl_2$ (F7), appears to be the best formulation because it did not cause any VF and maintained better inotropy than the F1 and F3 formulations. However the hemodynamic effects of the F5 formulation of Compound I, however, were equal to those of Visipaque, so a calcium concentration between F3 and F5 is preferred. Thus, in a particularly preferred embodiment the composition of the invention comprises 45 mM NaCl and 0.5 mM $CaCl_2$.

The intravenous and intra-arterial safety of this composition of Compound I was shown in a separate study. In this study the cardiovascular effects of Compound I in a composition of 45 mM NaCl and 0.5 mM $CaCl_2$ was assessed at three dose levels in vivo in an acute porcine model. In summary there were no overall changes to myocardial performance when the composition was administered via the intravenous and intra-arterial route. The study is further described in Example 3.

Generally, iodinated contrast media may cause late hypersensitivity reactions in susceptible patients from 1 hour to several days after exposure. These reactions are mainly non-serious skin eruptions such as macular, maculopapular and urticaria-like eruptions. Contrast media-induced delayed adverse reactions (DARs) such as skin eruptions appear to be caused by contrast media-reactive T cells that, upon recognizing the contrast media, proliferate and subsequently orchestrate an inflammatory reaction in the skin. The applicant has evaluated an in vitro T cell proliferation model designed to predict the relative frequency with which contrast media, such as Compound I, will cause late skin reactions in patients post-intravascular administration. Two contrast media, iodixanol and iohexol, with known rates of delayed skin reactions, and the new contrast medium, Compound I, was screened (2 and 5 mg I/mL) for in vitro T cell proliferation in $CD25^+$-depleted peripheral blood mononuclear cells from 100 donors representing world population HLA-DR frequencies. Positive T cell responses were evaluated according to published protocols and stimulation index values (positive response≥1.9). In vitro toxicity was tested by measuring cell viability of the first 10 donor samples incubated with test contrast media (5 mg I/mL). The results were that all major HLA-DR allotypes were represented with a frequency equivalent to the world population. No contrast media tested appeared to have a meaningful effect on cell viability. Compound I had fewer positive T cell proliferation donor samples compared with iodixanol and iohexol at both concentrations. For iodixanol and iohexol, T cell proliferation responses for most donors occurred on days 7 and 8; statistical significance favored a reduced proliferation response to Compound I on day 8. In conclusions the model successfully established the relative frequency with which contrast media caused in vitro T cell activation. The results correlated with reported frequency of late skin reactions with two marketed contrast media and identified a lower frequency for Compound I.

The results hence indicate that Compound I has the lowest capacity for stimulating in vitro T cell proliferation compared with iodixanol and iohexol. Given the more frequent association of DAR with dimeric contrast media, our finding that a non-ionic dimer closely related to iodixanol does not stimulate T-cell proliferation in vitro to the same extent as iodixanol, or indeed the same extent as the monomer iohexol, is of considerable interest. Because it is now known that T-cell proliferation underlies DAR, our data suggest that a dimeric structure per se may not in itself cause a greater frequency of T cell proliferation. The key structural difference between Compound I and iodixanol is that 2 acetyl groups in iodixanol have been replaced by 2 formyl groups in Compound I. This modification has an effect on the molecule's linker structure, conformation, and physicochemical behaviour, and surprisingly Compound I as a lower capacity for stimulating in vitro T cell proliferation than iodixanol and iohexol. Hence, a diagnostic composition according to the first aspects of the invention is expected to cause fewer late hypersensitivity reactions than commercialised contrast media such as Omnipaque™ (Iohexol) and Visipaque™ (Iodixanol).

Compound I can be prepared as outlined in WO 2009/008734. A general procedure is outlined on pages 16-20, and a specific method for preparation is provided in Example 1 of WO 2009/008734. The WO 2009/008734 application, with its description of a process for preparation is hereby incorporated by reference.

Compound I may exist in several isomeric forms due to chiral carbon atoms. In addition, the compound exhibits exo/endo isomerism due to the restricted rotation of the N—CO bond in the formyl function caused by the proximity of the bulk iodine atom. Both enantiomerically pure products as well as mixtures of optical isomers are included.

The diagnostic composition of the invention is in a ready to use concentration. Generally compositions in a ready to use form will have iodine concentrations of at least 100 mg I/ml, preferably at least 150 mg I/ml, with concentrations of at least 300 mg I/ml, e.g. 320 mg I/ml being preferred. The diagnostic composition preferably further includes pharmaceutically acceptable carriers or excipients. Examples of such are Ethylenediaminetetraacetic acid (EDTA) and tris(hydroxymethyl)amino methane (TRIS).

The diagnostic composition of the invention is preferably for use as an X-ray contrast media in X-ray diagnoses or X-ray imaging. The composition may be administered as a bolus injection or by infusion. Further, the composition may be administered by intravascular, intravenous or intra-arterial administration. Alternatively, the composition may also be administered orally.

In a third aspect, the invention provides the use of a Compound I

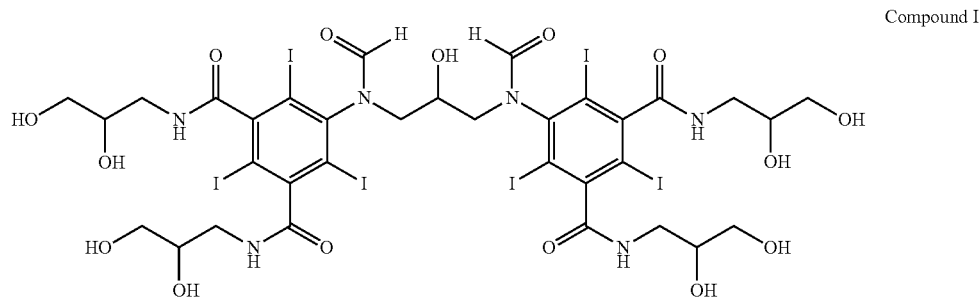 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound I for the manufacture of a diagnostic composition for use in x-ray diagnosis, wherein the composition comprises
a pharmaceutically acceptable carrier;
and dissolved therein a sodium compound and a calcium compound providing a sodium ion concentration of 40-50 mM and a calcium ion concentration of 0.1-0.7 mM.

In yet another aspect, the invention provides a method of diagnosis comprising administering a diagnostic composition of the invention to a human or animal body, examining the body with a diagnostic device and compiling data from the examination. In the method of diagnosis the body may also be preadministered with the diagnostic composition.

In yet another aspect, the invention provides a method of in vivo imaging detection comprising the following steps;
  i) administering a detectable quantity of the diagnostic composition of the invention;
  ii) allowing the administered composition to distribute;
  iii) detecting signals emitted by the compound I of the distributed composition,
  iv) generating an image representative of the location and/or amount of said signal.

The method of imaging is a method of X-ray imaging and in a preferred embodiment of this aspect, the method of detection is a method of coronary arteriography, and more preferably the diagnostic composition is administered as a bolus injection to the coronary arteries.

In yet another aspect, the invention provides a composition of the invention for use in x-ray imaging or diagnosis, such as in coronary arteriography.

BRIEF DESCRIPTION OF THE DRAWINGS

FIG. 1 depicts a comparison of the distribution of radioactivity in male and female Wistar rats at 48 hours post-administration of [$^{123}$I] labeled Compound I.

FIG. 2 depicts the frequency of ventricular fibrillation caused by injection of Mannitol, Mannitol+added sodium and calcium, Iodixanol+Mannitol, Visipaque™ and Ringer solution. Data taken from Chai et al.

FIG. 3 depicts the frequency of ventricular fibrillation caused by injection of compositions of Compound I, comprising different concentrations of calcium chloride, compared with injections of Visipaque. The injection volume was 25 ml over a period of 62.5 s and the solutions were selectively injected into the LAD.

FIG. 4 depicts the viscosity of Compound I at 20° C. and 37° C. versus concentration.

FIG. 5 depicts the effect of Compound I (with and without added Ca) and Visipaque on LVSP 45 to 70 seconds from the start of injection to the LAD of normal pigs normalised to Ringer Lacate (LR) injection.

FIG. 6 a) and b) depicts the effect on cardiovascular parameters following injection of 40 ml (5 ml/sec) of Ringer Lactate, Compound I, Visipaque or Iopamidol to the LAD of normal pigs.

EXAMPLES

Example 1

Physiochemical Properties, Acute Toxicity and Biodistribution Data for Compound I Protein Binding:

The binding of Compound I to human serum albumin (HSA) was determined using an equilibrium dialysis method. A stock solution of Compound I (5.0 mg/ml in phosphate buffered saline (PBS)) was mixed with citrate:human plasma in a ratio of 1:9. Equilibration was carried out in a Diachem Dianorm Dialyser against an aqueous phosphate buffered saline using a Diachem 10.17 MW cutoff 10000 membrane and was carried out for 25 hours. Analysis of the solutions was performed using an ICP-AES instrument. In addition, spiked PBS solutions were also equilibrated against citrated human plasma solutions to ensure that the equilibrium had been obtained. The binding of Compound I to human serum albumin was determined to be very low, 3.1±1.3%, confirming the negligible interaction of the substance with endogenous proteins. As a reference, the binding of iodixanol to HSA was determined to 0.4±0.9%.

Partition Coefficient.

As a measure of the hydrophilicity of Compound I, the partition coefficient between octanol and water was determined. Water (5 ml) containing the test substance (0.3 mg/ml) was shaken with 15 ml n-octanol until equilibrium had been obtained. The aqueous phase was separated by centrifugation and analyzed by HPLC (HP1100 equipped with a Discovery C18 column, 100×2.1 mm) using UV detection at 244 nm and a flow of 0.3 ml/min. Isocratic HPLC conditions were used, 8% acetonitrile in water (v/v). The octanol phase (12.5 ml) was extracted with water (0.75 ml) until equilibrium had been obtained and the phases were separated by centrifugation. The aqueous phase was analyzed by HPLC using the conditions detailed above. Both octanol and water were pre-saturated with water and octanol, respectively, before the partition coefficient experiments. The hydrophilicity of Compound I, as determined through the partition between octanol and water, showed that Compound I is very hydrophilic with a logP of −4.28. As a comparison, the corresponding logP of iodixanol was determined to −4.02. The reported literature value is −4.05. The increased hydrophilicity of Compound I compared to iodixanol is confirmed by its HPLC behavior.

Viscosity.

The viscosity of Compound I was determined at two different temperatures, 20° C. and 37° C. and three different concentrations, 246, 295 and 313 mgI/ml. The test solutions were isotonic through adjustment of the osmolality with NaCl and had been sterilized by autoclavation. The density of the solutions was determined using a Density meter, DMA58 (Anton Paar). A calibrated U-tube technique was used, where the time of fall was used as a measure of dynamic viscosity. The viscosity of compound I was determined at 20° C. and 37° C. at three different concentrations. The results are shown in FIG. 4. In comparison with Visipaque, the viscosity at 320 mgI/ml and 20° C. is similar, around 24 mPas.

Osmolality:

The osmolality of Compound I was determined at four different concentrations, 204, 254, 310 and 324 mgI/ml. A Vapro 5520 vapour pressure osmometer from Vapro Inc. was used. The osmolality of Compound I shows a relationship with the concentration which is close to linear.

The osmolality of Compound I at 320 mgI/ml is lower than that of iodixanol, 136 mOsm/kg vs 210 mOsm/kg at 320 mgI/ml.

Acute Toxicity:

Young adult male Sca:SD rats (Scanbur, Sweden), weighing 200±20 g, were injected intravenously at a rate of 1.2 ml/min with either Compound I (340 mgI/mL, 286 mosmol/kg), iodixanol (321 mgI/mL, 284 mosmol/kg), osmotic control mannitol (283 mosmol/kg), or saline (290 mosmol/kg), administered as 2 separate doses 4 hours apart. For the interim kill animals (day 2 post-treatment), Compound I and iodixanol were dosed at 8, 10 and 12.8 gI/kg, corresponding to total dose volumes of 23.7, 29.7 and 38.0 ml/kg, and 25, 31.3 and 40 ml/kg, respectively, whereas for mannitol and saline, the dose volume was 40 ml/kg. For the 7 day terminal kill animals, there were 4 dose groups; Compound I and iodixanol (12.8 gI/kg), and saline and mannitol (40 mL/kg). In all cases, each group included 8 animals.

The following evaluations were made during the study; clinical signs, body weights and blood for haematology and clinical chemistry on days 0, 2 and 7, and gross observations, organ weight and histomorphological examination of tissues from the animals killed by excess intravenous thiopental injection on days 2 or 7. The day of dosing was defined as Day 0. Clinical biochemistry parameters (Na, K, Cl, $PO_4$, Ca, AST, ALT, ALP, cholesterol, creatinine, CK, GGT, TG (triglyceride), total bilirubin, total protein, urea, albumin, LDH and GLDH were measured on a Beckman Synchron CX5 at 37° C. Haematology parameters (WBC, differential WBC, RBC, WBC/RBC ratio, Hgb, PLT, HCT, MCH, MCHC, MCV, MPV and RDW) were analyzed with an Abbott Cell-Dyn 3500 CS automated haematology analyzer. Kidneys from saline control and the 12.8 gI/kg Compound I and iodixanol groups were immerse fixed in 10% neutral buffered formalin, processed into paraffin wax, sectioned at a nominal thickness of 5 μm, stained with haematoxylin and eosin and examined by light microscopy.

The data were analysed by parametric one-way ANOVA, followed by Dunnett's post procedure test, using the 2 days and 7 days saline groups for comparison with the 2 days and 7 days iodixanol and Compound I groups. The statistical analysis was applied on day −1 (baseline), day 2 and day 7.

Biodistribution:

For each time point (2, 20 mins, 1, 2, 4, 24, 48 hours) 3 animals of each sex were anaesthetized with isoflurane. Each study animal received 2 injections within approximately 20 seconds. The first injection was a formulation of Compound I (non-radioactive) at ~320 mgI/ml, administered to give a total chemical dose of ~1.6 gI/kg via a specific tail vein (left or right). As soon as possible afterwards (within approximately 20 seconds) the radioactive [$^{123}$I] Compound I Test Item (~1 to ~8 MBq, up to 350 ug) was injected as an intravenous bolus to the opposite tail vein. This approach allowed the amount of radioactivity administered to be adjusted according to the dissection timepoint (study day 1, 2 or 3) without significantly altering the total chemical dose of Compound I. Animals were then placed in metabolism cages for the collection of urine and faeces until the appropriate time post-injection of labeled Compound I. At this time, animals were again anaesthetized with isoflurane and sacrificed by cervical dislocation. Selected organs and tissues (blood, kidneys, bladder and urine, lung, liver, stomach, small and large intestine, heart, testes, ovaries, uterus and faeces) were removed, along with the tail, which was assayed as the injection site. The amount of radioactivity in selected organs, tissues and excreta was then assayed using an automatic twin crystal gamma counter and analysis system.

Acute Toxicity Results:

There were no adverse clinical signs in rats treated with saline or mannitol, whereas in those treated with Compound I and iodixanol, mild to moderate depression and uncoordinated movements and weakness/inactivity was seen, as well as oedema and erythema of the extremities. These effects began 10-20 min after the first administration and lasted 2-3 h, but without a clear dose-response. Analyses of the haematology and clinical chemistry data indicated that there were no toxicologically significant adverse effects in any of the groups.

In the kidneys, the main treatment-related findings were cytoplasmic vacuolation of the proximal tubules, and in the glomeruli, dilatation of the Bowman's space containing proteinaceous material. On day 2, the severity of vacuolation was greater in those given iodixanol compared to Compound I. By Day 7, the severity of vacuolation was somewhat less compared to Day 2 in both groups, as was the Bowman's space dilatation and the presence of proteinaceous material.

TABLE 1

Summary of the major histomorphical findings in the kidneys:

| Group | No rats | Day of Necropsy | Test Item | Dose (gI/kg) | Proximal Tubule Vacuolation | | Glomerulus: Bowman's Space Dilatation | | Glomerulus: Bowman's Space Proteinaceous Material | |
|---|---|---|---|---|---|---|---|---|---|---|
| | | | | | Left Kidney | Right Kidney | Left Kidney | Right Kidney | Left Kidney | Right Kidney |
| 1 | 8 | 2 | Saline | — | 0, 0, 0, 0 0, 0, 0, 0 | 0, 0, 0, 0 0, 0, 0, 0 | 0, 0, 0, 0 0, 0, 0, 0 | 0, 0, 0, 0 0, 0, 0, 0 | 0, 0, 0, 0 0, 0, 0, 0 | 0, 0, 0, 0 0, 0, 0, 0 |
| 5 | 8 | 2 | Compound I | 12.8 | 3, 3, 3, 3 3, 3, 3, 3 | 3, 4, 3, 3 3, 3, 3, 3 | P, P, 0, P, 0, 0, 0, P | 0, 0, 0, 0, P, 0, P, 0 | P, P, 0, P, 0, 0, 0, P | 0, 0, 0, 0, P, 0, P, 0 |
| 8 | 8 | 2 | Iodixanol | 12.8 | 4, 4, 4, 4, 4, 4, 4, 4 | 4, 4, 4, 4, 4, 4, 4, 4 | P, P, 0, 0, P, 0, P, P | P, P, P, P, P, P, P, P | P, P, 0, 0, P, 0, P, P | P, P, P, P, P, P, P, 0 |
| 9 | 8 | 7 | Saline | — | 0, 0, 0, 0 0, 0, 0, 0 | 0, 0, 0, 0 0, 0, 0, 0 | 0, 0, 0, 0 0, 0, 0, 0 | 0, 0, 0, 0 0, 0, 0, 0 | 0, 0, 0, 0 0, 0, 0, 0 | 0, 0, 0, 0 0, 0, 0, 0 |
| 10 | 8 | 7 | Compound I | 12.8 | 3, 3, 2, 2, 2, 2, 3, 3 | 3, 3, 2, 2, 3, 2, 3, 3 | 0, 0, P, P, 0, 0, P, 0 | 0, P, 0, 0, 0, 0, 0, P | 0, 0, P, P, 0, 0, P, 0 | 0, P, 0, 0, 0, 0, 0, P |
| 11 | 8 | 7 | Iodixanol | 12.8 | 3, 3, 2, 2, 3, 3, 3, 3 | 3, 3, 2, 2, 3, 3, 3, 3 | 0, 0, 0, 0, P, 0, 0, 0 | 0, 0, 0, 0, 0, 0, P, 0 | 0, 0, 0, 0, P, 0, 0, 0 | 0, 0, 0, 0, 0, 0, P, 0 |

Key to findings:
0 = Not present;
P = Present;
1 = minimal;
2 = mild;
3 = moderate;
4 = marked;
5 = severe.

Biodistribution Results:

Following intravenous administration [$^{123}$I] labeled Compound I was rapidly excreted with >80% of injected dose (id) present in the bladder and urine 2 hours post-injection. Levels in blood decreased from 21% id at 2 minutes post-injection to 0.6% id 2 hours post-injection. There was a small but significant amount of excretion via the faecal route, which appeared slightly higher in female animals (14.3% id in the faeces) compared with male animals (8.2% id in the faeces) at 48 hours post-injection, although this difference was not statistically significant. Less than 2% id was retained in the body 48 hours post-injection of labeled Compound I, with approximately 0.5% retained in the kidneys, 0.1% retained in the liver and less than 1% in the remaining carcass (FIG. 1), all of which had further decreased from the 24-hour timepoint. This likely reflects the continued, slow excretion of the Compound I retained in the body following the initial, rapid excretion phase. There was no retention of radioactivity in the reproductive organs. Overall, the biodistribution profile of labeled Compound I was similar to other dimeric iodinated contrast agents.

Example 2

Comparison Studies

2a) Comparison of Cardiotoxicity of Visipaque™ and Diagnostic Compositions of Compound I in a Pig LAD Occlusion Model Reference is made to the study by Chai et al. (Acad. Radiol. 2004, 11, 583-593) where it was shown that a formulation of Iodixanol containing 19 mM NaCl and 0.3 mM CaCl$_2$ exhibits a lower frequency of ventricular fibrillation than Iodixanol alone. The study was carried out in pigs where the medium was injected directly into the left coronary artery (LCA) which had been previously occluded. It is clear from FIG. 2 that a formulation of Iodixanol containing 19 mM NaCl and 0.3 mM CaCl$_2$ exhibits a lower frequency of ventricular fibrillation than Iodixanol alone (P<0.01). In this case, no occurrence of ventricular fibrillation was observed on injection of Visipaque™. The dose given in these experiments was 20 ml at an injection rate of 2.0 ml/minute.

Since in the study by Chai et al. intracoronary injection of 20 ml iodixanol (formulated as Visipaque) was carried out over a 40-s injection time and no instances of VF occurred, we performed a study in which the injection volume was increased to 25 ml over a period of 62.5 s to increase the instances of VF for comparison purposes. In addition, the test and reference solutions were selectively injected into the left anterior descending coronary artery (LAD) in order to further increase the sensitivity of the model. The physical and chemical properties of the test solutions are provided in table 2 and results are presented in FIG. 3.

TABLE 2

Physical and chemical properties of test solutions

| Test agent | Iodine concentration (mg I/mL) | Electrolytes (mM) | |
|---|---|---|---|
| | | Na | Ca |
| F1: Compound I + NaCl + CaCl$_2$ | 320 | 45 | 0.1 |
| F3: Compound I + NaCl + CaCl$_2$ | 320 | 45 | 0.3 |
| F5: Compound I + NaCl + CaCl$_2$ | 320 | 45 | 0.7 |
| Iodixanol + NaCl + CaCl$_2$ (Visipaque) | 320 | 19 | 0.3 |

At this high injection volume, even Visipaque™ exhibited a significant frequency of ventricular fibrillation, 100% (FIG. 3).

However, to our surprise, the new X-ray contrast agent Compound I, when formulated with 45 mM NaCl and 0.1-0.7 mM CaCl$_2$, showed no occurrences of ventricular fibrillation (See FIG. 3 and Table 3 for details).

When comparing the results from the two different studies, an increase in the frequency of ventricular fibrillation from 0% to 100% is observed with Visipaque™. However, even at the high dose, the dimeric X-ray contrast Compound I in a diagnostic composition exhibits no ventricular fibrillation. The major difference is that Compound I has been formulated with 45 mM NaCl, which is significantly higher than that of Visipaque (19 mM). Although no significant effect was seen in VF, with calcium ion concentration between 0.1 and 0.7 mM on VF, there was a significant reduction in SAP and LVP when less calcium was present (Table 3).

TABLE 3

Hemodynamic changes at 50 s after start of injection, % of pre-injection value

|  | F1 | F3 | F5 | Visipaque |
|---|---|---|---|---|
| SAP | −18% ± 11 | −9% ± 7.2* | −4% ± 6.1†‡ | −5% ± 4.5†§ |
| LVP | −16% ± 10 | −7% ± 8* | −3 ± 7† | −4% ± 5† |
| dP/dt max | +10% ± 27 | +31% ± 38 | +34% ± 29 | +21% ± 10.8 |
| HR | −1% ± 1.0 | 0% ± 0.8 | −2% ± 3.0 | 0% ± 3.5 |

SAP: systolic arterial pressure (mm Hg)
LVP: left ventricular systolic pressure (mm Hg)
dP/dt max: maximum rate of LV pressure generation (mm Hg/s)
HR: heart rate (beats/min)
*P < 0.05 vs F1.
†P < 0.01 vs F1.
‡P < 0.05 vs F3.
§P < 0.01 vs F3.

These data indicate that the major factor influencing the frequency of ventricular fibrillation is the concentration of sodium chloride, while calcium has a significant effect on systolic arterial pressure and left ventricular systolic pressure.

2b: Comparison of Compound I in Compositions with and without Added CaCl$_2$ with Visipaque and Iopamidol The haemodynamic effects of compositions of Compound I with and without added CaCl$_2$ were compared to Visipaque and Iopamidol following selective administration to the LAD in normal pigs without balloon occlusion. The effects of each contrast media were normalised to any effects seen with an equivalent injection of Ringer Lactate solution, which acted as a volume and electrolyte—"ratio" control. There were a total of 12 pigs in this study, and each pig received a single CM injected 3 times at volumes of 10 ml (4 ml/sec), 20 ml (1 ml/sec) and 25 ml (0.4 ml/sec) (total of 9 CM injections in each pig). Each CM was either preceded or followed by a control injection of Ringer Lactate, and the order of each injection (volume) was randomised in each pig. Table 4 provides the amounts and ratios of sodium and calcium electrolytes used.

TABLE 4

| Electrolytes | Visipaque mM | Compound I mM | Compound I + CaCl$_2$ mM | Ringer Lactate mM or (Ratio) | Human Interstitial Fluid mM or (Ratio) |
|---|---|---|---|---|---|
| Na | 19 | 45 | 45 | 130 | 140 (135-145) |
| Ca | 0.3 | — | 0.5 | 3 | 1.2 (1.2-1.3) |
| Na/Ca | 63 | — | 90 | 43 | 117 |

At an injection volume of 25 ml Compound I in a composition without added CaCl$_2$ was associated with a reduction in LVSP between 45 and 70 seconds after injection (mean of −5.7 mm Hg normalised to Ringer Lactate) whereas Compound I in a composition with added CaCl$_2$ and Visipaque had little or no effect (−0.3 and +0.1 mm Hg normalised to Ringer Lactate respectively) (FIG. 5). The decrease in LVSP observed with the composition of Compound I without added CaCl$_2$ was significantly different to that with added CaCl$_2$, which was not significantly different to Visipaque. In addition, a corresponding response to Iopamidol injection could not be analysed since VF was observed in each case between approximately 27 and 50 seconds after the start of the 25 ml injection. These results indicate that the presence of 0.5 mM CaCl$_2$ in the composition of Compound I is beneficial and limits any negative effects on LVSP in a manner similar to Visipaque. In addition, the additional electrolytes present in the diagnostic composition of Compound I and Visipaque may lower the propensity for induction of VF compared with Iopamidol which has no added electrolytes.

2c: Comparison of a Composition of Compound I with Visipaque, Iopamidol and Ringer Lactate in Normal Pigs with a Fast Injection Rate In a further study the haemodynamic effects of Compound I in a composition with 45 mM NaCl and 0.5 mM CaCl$_2$ was compared to Visipaque and Iopamidol following selective administration to the LAD of normal pigs with a fast injection rate (5 ml/sec). Ringer Lactate was also studied as a volume and electrolyte "ratio" control. In total 3 pigs were studied, and each CM was administered twice to each pig in random order. The injection rate used was 5 ml/sec with a total injection volume of 40 ml. Table 5 provides the amounts and ratios of sodium and calcium electrolytes used.

TABLE 5

| Electrolytes | Visipaque mM | Compound I mM | Ringer Lactate mM or (Ratio) | Human Interstitial Fluid mM or (Ratio) |
|---|---|---|---|---|
| Na | 19 | 45 | 130 | 140 (135-145) |
| Ca | 0.3 | 0.5 | 3 | 1.2 (1.2-1.3) |
| Na/Ca | 63 | 90 | 43 | 117 |

Whilst Compound I and Visipaque injection did not induce changes in LVSP or dP/dt from baseline that were significantly different from Ringer Lactate administration, Iopamidol induced a significant decrease and increase in LVSP and dP/dt values respectively (FIG. 6, a) and b), respectively). LVSP was reduced by 9%±6 and dP/dt increased by 69%±16 following Iopamidol administration. This was in contrast to Ringer Lactate, Compound I and Visipaque injection, which were associated with a slight increase in LVSP (~5%) and a modest increase in dP/dt (up to ~30%). These results indicate that following fast injection into the LAD of normal pigs Compound I in a composition with 45 mM NaCl and 0.5 mM $CaCl_2$ had minimal effects on haemodynamic parameters similar to Visipaque or physiological Ringers solution. It is considered that the presence of electrolytes in the formulations of Compound I and Visipaque studied, which are more similar to the balanced composition of Ringer Lactate and the interstitial fluid, contributed to a superior maintenance of cardiac function compared with that following Iopamidol injection, which contains no added electrolytes.

Example 3

Intravenous and Intra-Arterial Safety of Diagnostic Composition of Compound I

The intravenous (i.v) and intra-arterial (i.a.) safety of a composition of Compound I was shown in a separate study (ref. B145095). In this study the cardiovascular effects of Compound I in a composition with 45 mM NaCl and 0.5 mM $CaCl_2$ was assessed at three dose levels in vivo in an acute porcine model.

Methods:

The composition was administered either intra-arterially or intravenously into groups of three animals at one of three dose levels (1-fold, 2-fold or 3-fold the standard volume of 2 ml/kg). Each animal also received an equivalent volume of Ringer-Lactate solution as a volume control. CV effects: heart rate (HR), pulse oximetry, electrocardiogram (ECG), aortic pressure (systolic, diastolic and mean), left ventricular end diastolic pressure (LVEDP) were assessed. Ultrasound/echocardiography to assess stroke volume, ejection fraction and cardiac contractility were also evaluated.

Results:

Evaluation of the preliminary data summary suggests that there were no important dose or route-related effects of Compound I on HR, pulse oximetry and ECG in the porcine heart. Pulse oximetry analysis showed oxygen saturation remained at approximately 98% throughout dosing. HR also remained within normal ranges. There were no Compound I-related rhythm disturbances: QT interval was within the normal range regardless of i.a. or i.v. dosing of Compound I. Similarly, little or no effect of Compound I was observed on aortic pressure (systolic, diastolic and mean) over the entire dose range. The changes in aortic pressure appeared similar whether Compound I was administered by the i.v. or i.a. route. There were slight increases in LVEDP with increasing doses of Compound I, the effect was similar whether Compound I was administered via i.v. or i.a. routes. In addition, increases in LVEDP were similar in magnitude to those seen following the administration of increasing volumes of Ringer-Lactate. Analysis of stroke volume, ejection fraction and cardiac contractility by echocardiography showed only a slight change in end diastolic volume (EDV), confirming any effects were volume related and not specific to Compound I administration.

Hence, there were no overall changes to myocardial performance when Compound I was administered via the i.a. or i.v. route. The minor changes in CV function parameters were attributed to the volume administered and not the test item Compound I, because similar effects were seen upon injection with Ringer Lactate solution. All myocardial parameters were within the normal ranges after intravenous or intraarterial administration of Compound I up to 3-fold the standard dose volume of 2 ml/kg.

What is claimed is:

1. A diagnostic composition comprising a Compound I

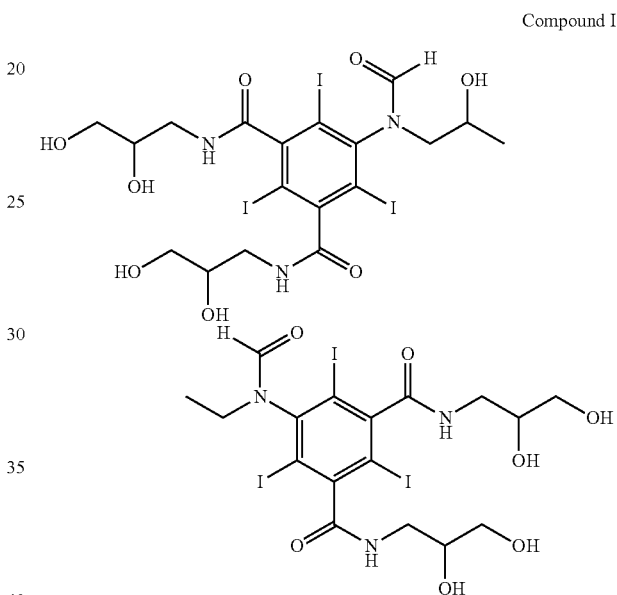

Compound I a pharmaceutically acceptable carrier;
and dissolved therein a sodium compound and a calcium compound providing a sodium ion concentration of 40-50 mM and a calcium ion concentration of 0.1-0.7 mM.

2. A diagnostic composition as claimed in claim 1 comprising a sodium compound providing a sodium ion concentration of 42-47 mM.

3. A diagnostic composition as claimed in claim 1 comprising a sodium compound providing a sodium ion concentration of 44-46 mM.

4. A diagnostic composition as claimed in claim 1 comprising a sodium compound providing sodium ion concentration of 45 mM.

5. A diagnostic composition as claimed in claim 1 comprising a calcium compound providing a calcium ion concentration of 0.3-0.6 mM.

6. A diagnostic composition as claimed in claim 1 comprising a calcium compound providing a calcium concentration of 0.4-0.5 mM.

7. A diagnostic composition as claimed in claim 1 comprising a calcium compound providing a calcium concentration of 0.5 mM.

8. A diagnostic composition as claimed in claim 1 wherein the ratio between sodium ion concentration and calcium ion concentration is between 63 and 117.

9. A diagnostic composition comprising a compound I

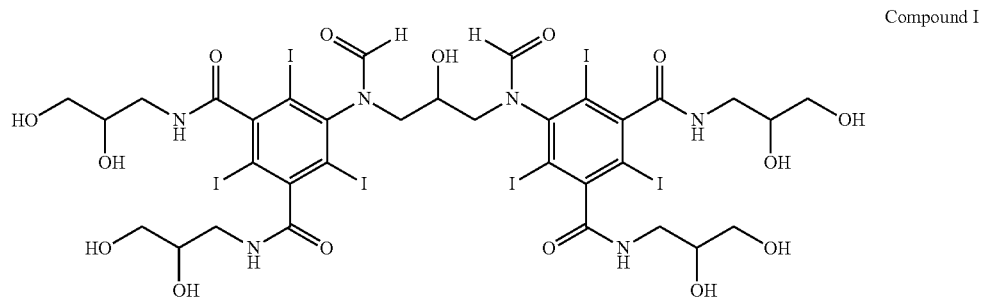 [SMILES: O=CN(CC(O)CN(C=O)c1c(I)c(C(=O)NCC(O)CO)c(I)c(C(=O)NCC(O)CO)c1I)c1c(I)c(C(=O)NCC(O)CO)c(I)c(C(=O)NCC(O)CO)c1I]

Compound I a pharmaceutically acceptable carrier;
and dissolved therein a sodium compound and a calcium compound wherein the ratio between sodium ion concentration and calcium ion concentration is between 40 and 45.

10. A diagnostic composition as claimed in claim 1 or claim 9 wherein the sodium compound and calcium compound are salts comprising counter ions selected from the group of chloride, sulphate, phosphate and hydrogen carbonate.

11. A diagnostic composition as claimed in claim 10 wherein the sodium compound is sodium chloride and the calcium compound is calcium chloride.

12. A diagnostic composition as claimed in claim 1 further comprising EDTA and/or TRIS.

13. A method of diagnosis comprising administering a diagnostic composition as claimed in claim 1 or claim 9 to a human or animal body, examining the body with a diagnostic device and compiling data from the examination.

14. A method of in vivo imaging detection comprising the following steps;
   i) administering a detectable quantity of the diagnostic composition as claimed in claim 1 or claim 9;
   ii) allowing the administered composition to distribute;
   iii) detecting signals emitted by the Compound I of the distributed composition,
   iv) generating an image representative of the location and/or amount of said signal.

15. A method as claimed in claim 14 wherein the method is a method of coronary arteriography.